US012593857B2

(12) United States Patent

Huchette-Defretin et al.

(10) Patent No.: US 12,593,857 B2

(45) Date of Patent: Apr. 7, 2026

(54) FERMENTED PEA SOLUBLES

(71) Applicant: ROQUETTE FRERES, Lestrem (FR)

(72) Inventors: Sophie Huchette-Defretin, Bethune (FR); Gabriel Macquart, Mont Bernanchon (FR)

(73) Assignee: Roquette Freres, Lestrem (FR)

( * ) Notice: Subject to any disclaimer, the term of this patent is extended or adjusted under 35 U.S.C. 154(b) by 876 days.

(21) Appl. No.: 17/757,659

(22) PCT Filed: Dec. 18, 2020

(86) PCT No.: PCT/FR2020/052547

§ 371 (c)(1),
(2) Date: Jun. 17, 2022

(87) PCT Pub. No.: WO2021/123675

PCT Pub. Date: Jun. 24, 2021

(65) Prior Publication Data

US 2023/0067393 A1 Mar. 2, 2023

(30) Foreign Application Priority Data

Dec. 19, 2019 (FR) .................................. FR1914964
Aug. 17, 2020 (FR) .................................. FR2008525

(51) Int. Cl.
*A23L 11/50* (2021.01)
*A23J 1/14* (2006.01)
(Continued)

(52) U.S. Cl.
CPC ............... *A23L 11/50* (2021.01); *A23J 1/148* (2013.01); *A23K 10/12* (2016.05); *A23K 20/105* (2016.05); *A23K 20/147* (2016.05); *A23K 20/163* (2016.05); *A23L 11/37* (2016.08); *A23L 33/125* (2016.08); *A23L 33/185* (2016.08); *C12N 1/205* (2021.05); *C12P 19/00* (2013.01); *C12P 19/12* (2013.01); *C12P 21/00* (2013.01); *C12R 2001/125* (2021.05)

(58) Field of Classification Search
CPC .............. A23L 11/50; A12J 1/14; A12J 1/148
See application file for complete search history.

(56) References Cited

U.S. PATENT DOCUMENTS 4,008,334 A 2/1977 Hansen et al.
4,216,235 A 8/1980 Dasek et al.
(Continued)

FOREIGN PATENT DOCUMENTS

EP 1400537 A1 3/2004
FR 2897239 A1 8/2007
(Continued)

OTHER PUBLICATIONS

Delbaere, F. (WO 2010/109093—Clarivate Analytics translation) (Year: 2010).*
(Continued)

*Primary Examiner* — Elizabeth Gwartney

(57) ABSTRACT

The invention relates to a water-soluble fermented pea extract. The invention also relates to a process for the preparation thereof and to the use thereof in the human and animal nutrition industry as well as in the pharmaceutical, nutraceutical and cosmetics industries.

15 Claims, 3 Drawing Sheets

(51) Int. Cl.

| | |
|---|---|
| ***A23K 10/12*** | (2016.01) |
| ***A23K 20/105*** | (2016.01) |
| ***A23K 20/147*** | (2016.01) |
| ***A23K 20/163*** | (2016.01) |
| ***A23L 11/30*** | (2016.01) |
| ***A23L 33/125*** | (2016.01) |
| ***A23L 33/185*** | (2016.01) |
| ***C12N 1/205*** | (2026.01) |
| ***C12P 19/00*** | (2006.01) |
| ***C12P 19/12*** | (2006.01) |
| ***C12P 21/00*** | (2006.01) |
| *C12R 1/125* | (2006.01) |

(56) References Cited

U.S. PATENT DOCUMENTS

| | | | |
|---|---|---|---|
| 5,651,967 A | 7/1997 | Rohde, Jr. et al. | |
| 6,159,715 A | 12/2000 | Porter et al. | |
| 2004/0198965 A1 | 10/2004 | Mollee et al. | |
| 2015/0157676 A1* | 6/2015 | Delbaere | A61P 31/04 426/655 |

FOREIGN PATENT DOCUMENTS

| | | | |
|---|---|---|---|
| WO | 2010/109093 | A1 | 9/2010 |
| WO | 2013011216 | A1 | 1/2013 |
| WO | 2014/118449 | A1 | 8/2014 |

OTHER PUBLICATIONS

Labia Irene Ivette Ou Oba, et al. "Degradation of polysaccharides and non-digestible oligosaccharides by Bacillus subtilis and Bacillus pumilus isolated from Soumbala. a fermented African locust bean (*Parkia biglobosa*) food Condiment", European Food Research and Technology, Springer, Berlin Heidelberg, vol. 224, No. 6, Aug. 2, 2006 (Aug. 2, 2006), pp. 689-694 ISSN: 1438-2385, XP 019488853; whole document.

Mulyowidarso R K, et al., "Changes in the Concentration of Carbohydrates During the Soaking of Soybeans for Tempe Production", International Journal of Food Science and Technology, Blackwell Scientific Publications, Oxford, GB, vol. 26, No. 6, Jan. 1, 1991 (Jan. 1, 1991), pp. 595-606 ISSN: 0950-5423, XP001015396; whole document, figure 4.

* cited by examiner

FERMENTED PEA SOLUBLES

CROSS-REFERENCE TO RELATED APPLICATIONS

This application is a National Stage Application of PCT/FR2020/052547 filed Dec. 18, 2020, which claims priority from French Patent Application No. 1914964 filed on Dec. 19, 2019 and French Patent Application No. 2008525 filed on Aug. 17, 2020. The priority of said PCT and French Patent Applications are claimed. Each of the prior mentioned applications is hereby incorporated by reference herein in its entirety.

BACKGROUND OF THE INVENTION

The present invention relates to a water-soluble fermented pea extract the nutritional composition of which is optimized, limiting the losses of raw material and recovering as much of the water-soluble fraction as possible. The invention also relates to the process for the preparation thereof and to the uses thereof in the human and animal nutrition industries as well as in the pharmaceutical, nutraceutical and cosmetics industries.

The present invention also relates to a novel strain of *Bacillus subtilis*, especially useful for obtaining a water-soluble fermented pea extract.

Leguminous plants constitute a raw material of choice for the food industry, especially for consumption after cooking, but also for the production of proteins, of starch especially rich in amylose, of fibers and of starch derivatives such as glucose syrups, maltodextrin, dextrose or isoglucose.

These products find outlets in various fields, such as the adhesive or paper sectors, but especially in the food sector, where the nutritional interest of leguminous plants, both in human and animal food, has been amply demonstrated. Among these, pulse plants, such as beans, peas and broad beans, are widely used for their energy and protein content. Dry pea seeds are indeed rich in carbohydrates, substantially made up of starch as well as sucrose and oligosaccharides, in proteins (high lysine content) and in fibers.

Despite their nutritional benefits, leguminous plants such as dry peas have poor digestibility, which often requires soaking them in an acidic medium and/or with the presence of sodium bicarbonate before cooking them and consumung them. This disadvantage is mainly attributed to their significant content of alpha-galactosyl oligosaccharides (or GOS) consisting of D-galactose, D-glucose and D-fructose units. Indeed, these oligosaccharides, which are not digestible by human enzymes (which are unable to break down their alpha 1,6-galactosidic and 1-3/1-4 fructosidic bonds), are transported intact to the colon where they provide a substrate for the fermentation of bacteria of the intestinal microbiota, causing flatulence phenomena. This phenomenon has especially been attributed, according to some authors, in the case of beans (*Phaseolus vulgaris*), to the fructose terminal unit of the raffinose they contain (MYHARA R M et al., Can. Inst. Food Sci. Technol. J., Vol. 21, no. 3, pages 245-250, 1988).

These oligosaccharides are therefore generally eliminated either by agronomic selection of lines (especially of soybean or bean) with reduced content of such oligosaccharides (BURBANO C. et al., J. Sci. Food Agric., Vol. 79, pages 1468-1472, 1999), either by physical separation and elimination, or by enzymatic hydrolysis (using an alpha-galactosidase) or fermentative hydrolysis, generally carried out prior to the consumption of these leguminous plants, but also by administration of food supplements made up of enzymes intended to hydrolyze these oligosaccharides into digestible compounds, before they arrive in the colon (U.S. Pat. No. 5,651,967).

Document U.S. Pat. No. 4,008,334 thus proposes a process for eliminating soluble carbohydrates from vegetable proteins, especially from soybeans, including raffinose and stachyose, by enzymatic digestion using a baker's yeast. It is interesting to note that in table 1 of this document, *Bacillus subtilis* is described as being incapable of hydrolyzing raffinose and stachyose. Likewise, document U.S. Pat. No. 4,216,235 suggests the utilization of a *Saccharomyces uvarum* yeast to break down the oligosaccharides of soybeans, including the melibiose and the manninotriose. These methods, although perfectly functional, result in the total hydrolysis of the oligosaccharides, which are however very useful in human and animal nutrition.

Document US 2004/0198965 suggests using the oligosaccharides, present especially in soybean seeds, for the synthesis of D-galactose.

More specifically for the pea, document WO2010/109093 proposes the utilization of an invertase in order to defructosylate the oligosaccharides. The GOS are thus preserved and recovered by this solution. However, the released fructose remains free in solution. This sugar is often criticized in nutritional terms, and is even problematic for some consumers, for example such as consumers with hereditary fructose intolerance (HFI). HFI is an autosomal recessive disorder related to fructose metabolism. It results from a deficiency in the activity of the hepatic fructose-1-phosphate aldolase enzyme and leads to gastrointestinal disorders and postprandial hypoglycemia after fructose ingestion. It is therefore necessary to get rid of them, by adding costly and time-consuming purification steps. In addition, the proteins eliminated as a preamble to the defructosylation reaction are also to be recovered separately. This process is therefore complex, and difficult to commercialize because of the different fractions generated.

BRIEF SUMMARY OF THE INVENTION

The invention aims to propose an alternative solution for recovering these water-soluble pea fractions. Specifically, it became apparent to the Applicant that the water-soluble pea fractions can be recovered by being fermented using a very specific protocol by certain microorganisms. The invention described hereunder thus makes it possible to contemplate a recovery of the water-soluble extracts, in a single integral fraction, and using a straightforward and natural process.

The invention relates to a water-soluble fraction extracted from leguminous plants comprising between 10% and 30% of defructosylated oligosaccharides, preferentially between 10% and 25%, preferentially between 15% and 25%, even more preferentially between 20% and 22%, and between 20% and 40% of proteins, preferentially between 25% and 35%, even more preferentially 30%, the percentages being expressed in dry weight relative to the total weight of solids.

The invention also relates to the process for obtaining this water-soluble fraction extracted from leguminous plants comprising the following steps:

1—Obtaining a water-soluble fraction of leguminous plants

2—Optionally, desalinating the water-soluble fraction

3—Fermenting the water-soluble fraction extracted from leguminous plants using a microorganism of the *Bacillus* genus, preferentially *Bacillus subtilis*

4—Optionally, eliminating the microorganism

5—Optionally, bacteriologically stabilizing the water-soluble fraction thus obtained.

The invention finally relates to the use of this water-soluble fraction of leguminous plants according to the invention in industry, particularly in the human and/or animal nutrition industries.

Another object of the invention is also a strain of *Bacillus subtilis* as deposited with the CNCM on May 28, 2020 under number 1-5515, as well as the different uses of such a strain.

DETAILED DESCRIPTION OF THE INVENTION

Figure 1:
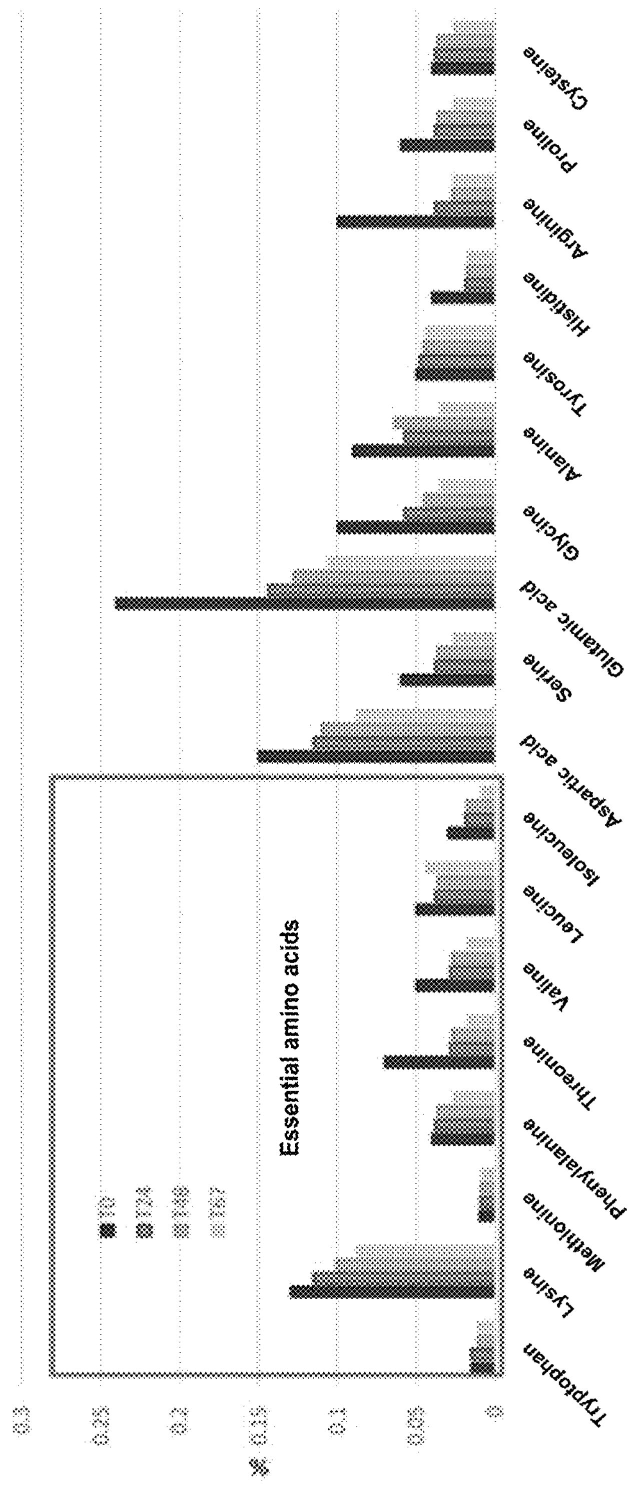
FIG. 1 shows the quantification of the amino acids during Example 3.
Figure 2:
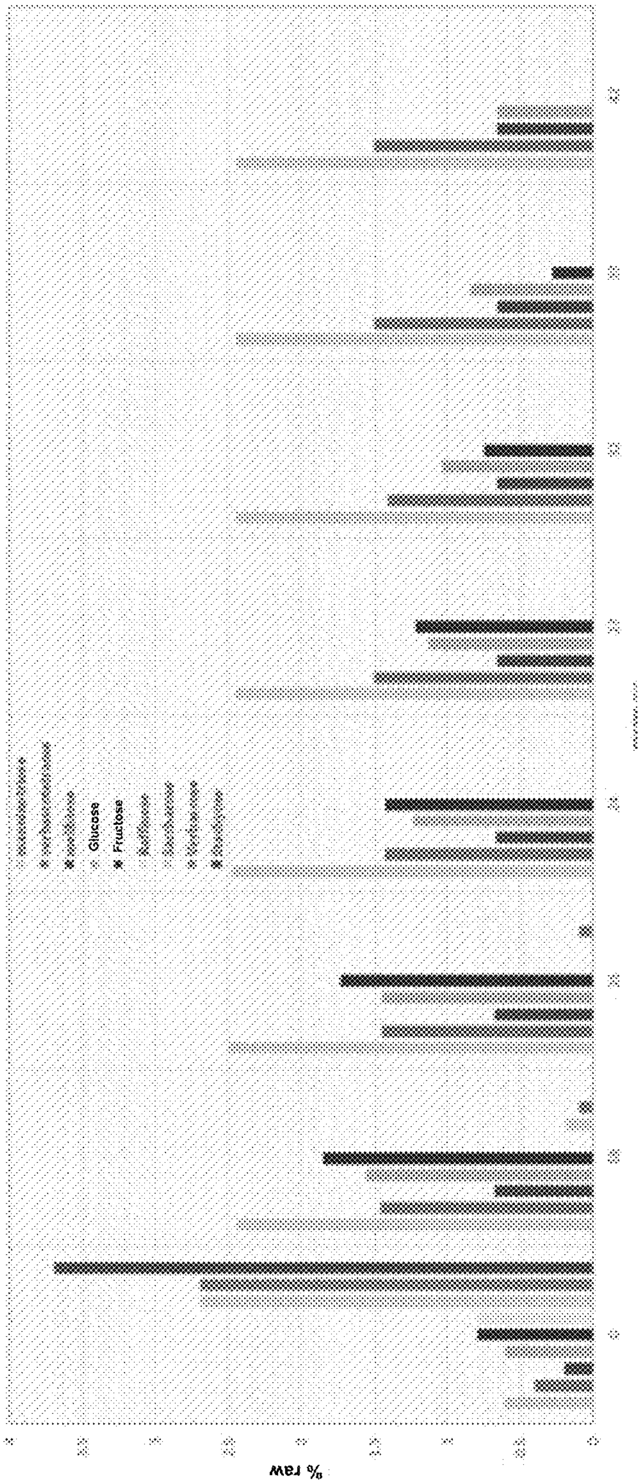
FIG. 2 shows the quantification of the various sugars during Example 4.
Figure 3:
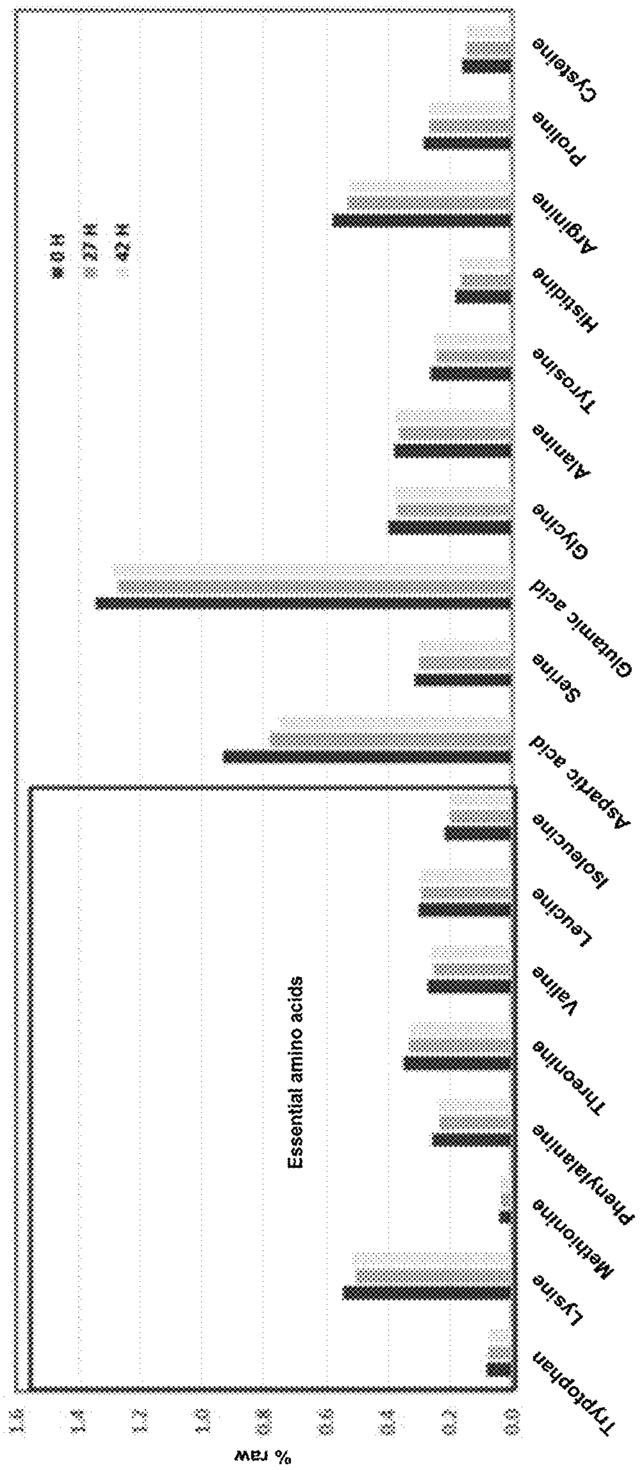
FIG. 3 shows the quantification of the amino acids during Example 4.

The first object of the invention is thus a water-soluble fraction extracted from leguminous plants comprising between 10% and 30% of defructosylated oligosaccharides, preferentially between 10% and 25%, preferentially between 15% and 25%, even more preferentially between 20% and 22%, and between 20% and 40% of proteins, preferentially between 25% and 35%, even more preferentially 30%, the percentages being expressed in dry weight relative to the total weight of solids.

The expression "water-soluble fraction", for the purposes of the present invention, means the residual aqueous fraction after the extraction of the starch, pulps (also referred to as internal fibers) and of the proteins of globulin type derived from seeds of leguminous plants, using a "wet" fractionation process. Such a process is, for example, the process described by the applicant in patent application EP1400537, which is incorporated herein by reference. This process makes it possible to obtain water-soluble pea fractions and pea pulps (cf. paragraphs 105 and 106). It can be modified by adding, for example, a step of soaking, of toasting (heating of the grains to dryness). This residual water-soluble fraction of a leguminous plant consists primarily of proteins that are soluble at an acidic pH, belonging mainly to the group of albumins, and also various water-soluble compounds such as sugars including GOS and salts. The residual soluble fraction of a leguminous plant may also undergo a heat treatment, which makes it possible to remove anti-nutritional factors such as trypsin inhibitors.

The expression "leguminous plant", for the purposes of the present invention, means the family of dicotyledonous plants of the Fabales order. This is one of the largest flowering plant families, third after Orchidaceae and Asteraceae in terms of number of species. It contains approximately 765 genera, bringing together more than 19,500 species. Several leguminous plants are important crop plants, including beans, peas, *faba* bean, lupin, bean, chickpea, peanut, cultivated lentil, cultivated alfalfa, various clovers, broad beans, carob, licorice.

Preferably, the leguminous plants are selected from the list consisting of pea and *faba* bean, even more preferentially of pea.

The term "pea" is considered here in its broadest accepted use and includes in particular all the varieties of "smooth pea" and "wrinkled pea" and all the mutant varieties of "smooth pea" and "wrinkled pea", regardless of the uses for which said varieties are usually intended (human food, animal feed and/or other uses). The term "pea" in the present application includes pea varieties belonging to the *Pisum* genus and more particularly to the species *sativum* and *aestivum*. Said mutant varieties are in particular those named "r mutants", "rb mutants", "rug 3 mutants", "rug 4 mutants", "rug 5 mutants" and "lam mutants" as described in the article by C-L HEYDLEY et al., entitled "Developing novel pea starches" Proceedings of the Symposium of the Industrial Biochemistry and Biotechnology Group of the Biochemical Society, 1996, pages 77-87.

The term "*faba* bean" is intended to mean the group of annual plants of the species *Vicia faba*, belonging to the group of leguminous plants of the Fabaceae family, Faboideae subfamily, Fabeae tribe. A distinction is made between Minor and Major varieties. In the present invention, wild-type varieties and those obtained by genetic engineering or varietal selection are all excellent sources.

The term "oligosaccharides", for the purposes of the present invention, means the oligomers formed from a number n of oses (monosaccharides) by alpha or beta glycosidic bond. By convention the number n varies from 3 to 10. Here, they are placed between the simple oses (n=1) and the polyosides (polysaccharides) (n>10). However, this limit of 10 units is not totally fixed and polyosides with a degree of polymerization of 11 to 25 are often assimilated to them. The oligosides comprising 2 oses are the diholosides (sucrose), 3 oses the triholosides (raffinose, melezitose) and 4 oses the tetraholosides (stachyose). The oligosides can be linear (stachyose), branched or cyclic (cyclodextrin).

Preferably, the water-soluble fraction according to the invention comprises defructosylated oligosaccharides selected from the list containing melibiose, manninotriose and verbascotetraose.

The term "melibiose", for the purposes of the present invention, means the diholoside consisting of a galactose unit bonded to a glucose unit by an $\alpha(1\rightarrow6)$ osidic bond.

The term "manninotriose", for the purposes of the present invention, means the triholoside consisting of the chain of one galactose unit bonded by an $\alpha(1\rightarrow6)$ osidic bond to another galactose unit, itself bonded to a glucose unit by another $\alpha(1\rightarrow6)$ bond.

The term "verbascotetraose", also referred to as "manninotetraose", for the purposes of the present invention, means the tetraholoside consisting of the chain of three galactose units bonded by $\alpha(1\rightarrow6)$ osidic bonds, the third galactose unit being itself bonded to a glucose unit by another $\alpha(1\rightarrow6)$ bond.

It is remarkable according to the invention that the oligosaccharides traditionally present in the water-soluble fraction of pea (raffinose, stachyose and verbascose) are completely defructosylated, enriching in defructosylated oligosaccharides (melibiose, manninotriose and verbascotetraose). In addition, the free fructose content is reduced relative to the initial content, despite the defructosylation. Without being bound by any theory, the strain described in the paragraphs below, which performs the defructosylation, must consume it again. The advantage over the prior art, in particular WO2010/109093, is that in a single step the GOS are defructosylated and the fructose is eliminated. The food industry therefore has at its disposal a water-soluble fraction the GOS of which are defructosylated and with a reduced fructose content.

Any method well known to a person skilled in the art for quantifying these defructosylated oligosaccharides is suitable for the purposes of the present invention. Chromatographic methods are preferred. Preferably, the person skilled in the art will use the HPAEC-PAD amperometric assay method and in particular with the following equipment:

The Dionex Carbopac PA1 4*50-mm precolumn-Ref. 43096

The Dionex Carbopac PA1 4*250-mm column-Ref. 35391

The detector is of the PAD type, precisely gold cell

The eluents are:

Solvent A/NaOH 0.1M: Stir 4 liters of water under Helium (flow rate: 100 ml/min) for 15 min. Add 20 ml of 50% NaOH. Stir again under helium at 40 ml/min.

Solvent B/NaOH 0.1M+0.5M sodium acetate Weigh 82 g of Na acetate directly in the canister. Add 2 l of H2O. Stir under helium (flow rate: 100 ml/min) for 15 min then add 10 ml of 50% NaOH, stir again under helium. The helium flow rate can be lowered to 40 ml/min.

Standards are used to calibrate the HPLC and in particular:

| Reagents | Reference |
|---|---|
| Melibiose | Fluka ref. 63630 |
| Raffinose | Sigma ref. R-0514 |
| Stachyose | Sima ref. S-4001 |
| Verbascose | Fluka ref. 56217 |

An internal standard is also used: Panose ref. SIGMA P-2407 60 mg in 100 ml water.

The injected volume is 5 μl at a temperature of 15° C. The analysis time is 90 min with a column temperature of 30° C. and an injector sensitivity of 300 nC or 5 μA The chromatographic elution conditions are as follows:

| Time (min) | Flow rate (ml/min) | Solvent A | Solvent B |
|---|---|---|---|
| 0 | 0.5 | 98 | 2 |
| 60 | 0.5 | 95 | 5 |
| 65 | 0.5 | 70 | 30 |
| 65.05 | 0.5 | 0 | 100 |
| 75 | 0.5 | 0 | 100 |
| 75.05 | 0.5 | 98 | 2 |
| 90 | 0.5 | 98 | 2 |

The oxidation program of the PAD detector is as follows:

| Time (min) | Potential | Integration |
|---|---|---|
| 0 | +0.05 | |
| 0.20 | +0.05 | Start |
| 0.40 | +0.05 | End |
| 0.41 | +0.75 | |
| 0.60 | +0.75 | |
| 0.61 | −0.15 | |
| 1.0 | −0.15 | |

The calibration is carried out by preparing 2 curves according to the table hereunder.

| Amount in mg | Melibiose q.s. 50 ml | Raffinose q.s. 25 ml | Stachyose q.s. 25 ml | Verbascose q.s. 25 ml |
|---|---|---|---|---|
| T1 | 10 | 5 | 5 | 5 |
| T2 | 25 | 10 | 10 | 10 |
| T3 | 50 | 15 | 15 | 15 |

-continued

| Amount in mg | Melibiose q.s. 50 ml | Raffinose q.s. 25 ml | Stachyose q.s. 25 ml | Verbascose q.s. 25 ml |
|---|---|---|---|---|
| T4 | 75 | 25 | 25 | 25 |
| T5 | 100 | | | |

Take 1 ml of control (from the 2 curves)+1 ml internal standard, q.s. 20 ml of water.

Weigh the amount in mg of sample, add 1 ml of internal standard and adjust to 20 ml of water.

Filter on GxF/GHP 0.45 μm ref. 4559T.

Advantageously, the water-soluble fraction according to the invention contains less than 2%, preferably between 0.25% and 1%, even more preferentially between 0.5% and 0.75% by weight of fructose, the percentages being expressed by weight relative to the total weight of solids.

Any method well known to the person skilled in the art for quantifying fructose is suitable for the purposes of the present invention. Enzymatic methods are preferred. The fructose can thus be titrated by HPLC chromatographic method. Preferably, a person skilled in the art would use the following method:

The glucose content titrated by this method must be less than 1 g/l, the same as for the fructose content, the amounts of glucose+fructose must be less than 1 g/l. If not, a preliminary dilution will be carried out and taken into account in the final calculation The principle is as follows:

Hexokinase (HK) catalyzes the phosphorylation of glucose and fructose by adenosine-5-triphosphate (ATP) at pH 7.6.

In a reaction catalyzed by glucose-6-phosphate dehydrogenase (G6P-DH), the glucose-6-phosphate formed (G6P) is specifically oxidized in the presence of nicotinamide adenine dinucleotide phosphate (NADP) to gluconate-6-phosphate, with formation of reduced nicotinamide adenine dinucleotide phosphate (NADPH).

$$\text{D-glucose} + \text{ATP} \xrightarrow{\text{HK}} \text{G-6-P} + \text{ADP}$$

$$\text{D-fructose} + \text{ATP} \xrightarrow{\text{HK}} \text{F-6-P} + \text{ADP}$$

$$\text{G-6-P} + \text{NADP}^{+} \xrightarrow{\text{G6P-DH}} \text{Gluconate-6-Phosphate} + \text{NADPH} + \text{H}^{+}$$

The amount of NADPH formed during the reaction is proportional to the amount of glucose.

At the end of the reaction, the fructose-6-P is transformed into glucose-6-P by the phospho-glucose isomerase.

$$\text{F-6-P} \underset{}{\overset{\text{PGI}}{\rightleftharpoons}} \text{G-6-P}$$

The G-6-P formed in turn reacts with the NADP forming gluconate-6-phosphate and NADPH. The amount of NADPH formed is measured again. It is proportional to the amount of fructose.

The reagents are as follows:

Standard solution of glucose and fructose at 1 g/l: Prepare a single standard containing both sugars at a concentration of 1 g/l.

Triethanolamine buffer pH 7.6: In a 500 ml beaker, weigh 88.45 g triethanolamine hydrochloride, 1,185 mg NADP (Roche ref. 240,354), 2,960 mg ATP (Roche ref. 127,523) and 1,250 mg MgSO4, 7H2O. Adjust the pH to 7.6 with 4N NaOH. Adjust to 500 ml with water.

Hexokinase (HK): Roche reference 127,825. Use as is.

Phosphoglucose-isomerase (PGI) Roche reference 128, 139. Use as is.

The procedure is as follows:

The reaction is done directly in the spectrophotometer cuvettes.

In each cuvette, introduce: 1 ml buffer solution, 1.9 ml water and 100 μl sample or 25 μl standard solution (+75 μl water)

Mix. Wait 5 minutes and measure the absorbance at 340 nm ($A_0$).

Add 20 μl hexokinase.

Mix. Wait until the end of the reaction (about 10 minutes) then read the absorbance at 340 nm ($A_1$).

Add 20 μl phosphoglucose isomerase (3-4).

Mix. Wait until the end of the reaction (about 10 minutes) then read the absorbance at 340 nm ($A_2$).

If the glucose content of the solution to be titrated is very low, increase the test specimen by replacing the water with the sample.

The same applies to fructose, but the glucose concentration of the solution to be analyzed must be taken into account.

The glucose concentration in g/l of the solution to be titrated is calculated according to the formula:

$$C = \frac{\lfloor (A_1 - A_0)_{ech} - (A_1 - A_0)_{blanc} \rfloor \times 0.5441}{6.3 \times v}$$

with v=volume of the sample test specimen in ml

The fructose concentration in g/l of the solution to be titrated is calculated according to the formula:

$$C = \frac{\lfloor (A_2 - A_1)_{ech} - (A_2 - A_1)_{blanc} \rfloor \times 0.5477}{6.3 \times v}$$

with v=volume of the sample test specimen in ml

In order to perform the fructose assay, it is necessary to perform the glucose assay first. The difference in absorbance for the glucose should not exceed 1.

When the glucose/fructose ratio in a sample exceeds 80/20, it is necessary, before performing the fructose assay, to destroy the glucose present by the action of the glucose oxidase (GOD) and the catalase in the presence of oxygen (see protocol hereunder).

Advantageously, the water-soluble fraction according to the invention contains less than 2%, preferably between 0.25% and 1%, even more preferentially between 0.5% and 0.75% by weight of lactate, the percentages being expressed by weight relative to the total weight of solids.

Lactic acid (or lactate) is a well-known carboxylic acid consisting of a carbon skeleton of 3 and having a hydroxyl function on its central carbon. It is often produced during fermentation of microorganisms when oxygen is lacking (e.g. in anaerobic conditions) and the metabolism of the fermented strain enters a so-called fermentative mode. The method for producing the water-soluble fraction according to the invention makes it possible to limit the production of this acid, which is undesirable in several food formulations if its content is too high.

Any method well known to the person skilled in the art for quantifying the lactic acid is suitable for the purposes of the present invention. Chromatographic methods are preferred. Preferably, a person skilled in the art would use the following method:

The amount of lactic acid is determined by HPLC in isocratic mode with:

AG11-HC pre-column—Dionex—Ref. 52962

AS11-HC column—Dionex—Ref. 52960 detector: conductivity meter

The eluents are:

A: Milli-Q purified water (under helium)

B: Dionex potassium hydroxide cartridge—Ref. 58900

A commercial standard of lactic acid (DL-lactic acid (sodium salt) Fluka—Ref. 71720) and an internal standard (trifluoroacetic acid (sodium salt) (400 mg/l solution) Sigma Ref. T-0757) are used to calibrate the HPLC.

The calibration is done with 5 points, weighing between 5 and 120 mg of control lactic acid q.s. 500 ml of water. Take 0.5 ml of each solution, add 0.5 ml of internal standard and adjust to 20 ml with 1 mM sodium hydroxide. Plot the calibration curve by height The chromatographic elution conditions are as follows (the molarity of eluent B is carried out by dilution with eluent A):

| Time (min) | Flow rate (ml/min) | Molarity B (mmol/l) |
|---|---|---|
| 0 | 1.5 | 1.5 |
| 15 | 1.5 | 1.5 |
| 28 | 1.5 | 12 |
| 48 | 1.5 | 28 |
| 60 | 1.5 | 40 |
| 60.1 | 1.5 | 60 |
| 67 | 1.5 | 60 |
| 67.1 | 1.5 | 1.5 |

Volume injected: 25 μl,

Injector T°: 10° C.

Analysis time: 77 min

ASRS: 300 mA

Column T°: 36° C.

Even more preferably, the water-soluble fraction according to the invention contains between 20% and 40% of proteins characterized as albumins, preferentially between 25% and 35%, even more preferentially 30%, the percentages being expressed in weight relative to the total weight of solids.

The term "albumin", for the purposes of the present invention, means proteins that are soluble in pure water. Pea albumins, which are present in pea proteins at about 20%, are mainly divided into two families named PA1 and PA2.

The albumins present in the water-soluble fraction according to the invention have a remarkably preserved amino acid profile, providing a very interesting source of amino acids. As will be exemplified below, it is the process of the invention, in particular the management of oxygenation, which makes it possible to simultaneously guarantee defructosylation, while preserving this almost identical profile, with the exception of the arginine that will be converted into agmatine.

Any method well known to the person skilled in the art for quantifying the protein content is suitable for the purposes of the present invention. Preferably, a person skilled in the art would use the following method referred to as "N6.25":

Assay of the total nitrogen using the Kjeldahl or Dumas method, preferentially Dumas. The expression of this nitrogen being in grams of nitrogen per total weight of the sample Multiplication of the previously titrated nitrogen content by the coefficient 6.25

Preferably, the soluble fraction according to the invention has proteins, preferentially albumins, the degree of hydrolysis of which, or DH, is less than 20, preferentially less than 18, even more preferentially less than 15

The expression "degree of hydrolysis" for the purposes of the present invention means the percentage ratio between the amount of amine (or carboxylic) functions of the free amino acids and the total amount, including the free functions and those engaged in a peptide bond (chemical bond characteristic of proteins resulting from the association of a carboxylic function of a first amino acid and an amine function of a second). For a protein composition consisting of the chain of all its amino acids and thus having only one free amine function and one free carboxylic function, this degree of hydrolysis will be 0%. Conversely, for a protein composition in which the same amino acids are all "free", that is their two amine and carboxylic functions are not involved in peptide bonds, this degree of hydrolysis will be 100%.

There are several methods for quantifying the degree of hydrolysis. They all consist mainly of the colorimetric assay of the free amine (or carboxylic) functions, followed by the performance of a hydrolysis aimed at destroying all the peptide bonds and finally of a colorimetric assay of the total amine (or carboxylic) functions. The calculated percentage of the free amines (or carboxyls) to the total amines gives the degree of hydrolysis. It is possible to use any well-known method such as the so-called TNBS method or the OPA method. In the present invention, the OPA method is preferred, a measurement procedure for which is described hereunder:

The content of amino nitrogen (free $NH_2$) is determined first of all on the sample of proteins according to the invention with the MEGAZYME kit (reference K-PANOPA). The content of protein nitrogen (total nitrogen) of the sample is also determined. It is then possible to calculate the degree of hydrolysis.

Determining the Content of Amino Nitrogen:

The "amino nitrogen" groups of the free amino acids in the sample react with the N-acetyl-L-cysteine and ophthaldialdehyde (OPA) to form isoindole derivatives.

The amount of isoindole formed during this reaction is stoichiometric with the amount of free amino nitrogen. It is the isoindole derivative which is measured by the increase in absorbance at 340 nm.

A test specimen P*, exactly weighed, of the sample to be analyzed is introduced into a 100 ml beaker. This test specimen will be from 0.5 to 5.0 g relative to the amino nitrogen content of the sample. Approximately 50 ml of distilled water is added, homogenization is carried out and the mixture is decanted into a 100-ml graduated flask. 5 ml of 20% sodium dodecyl sulfate (SDS) are added, and the mixture is supplemented with distilled water to reach a volume of 100 ml. Stirring is carried out for 15 minutes with a magnetic stirrer at 1000 rpm. A solution no. 1 is prepared by dissolving a tablet from bottle 1 of the Megazyme kit in 3 ml of distilled water and stirring is carried out until it is completely dissolved. It is necessary to provide one tablet per test. Solution no. 1 is prepared immediately before use.

A blank, a standard and a sample are directly prepared in the cuvettes of the spectrophotometer under the following conditions:

blank: introduce 3.00 ml of solution no. 1 and 50 μl of distilled water standard: introduce 3.00 ml of solution no. 1 and 50 μl of bottle 3 of the Megazyme kit sample: introduce 3.00 ml of solution no. 1 and 50 μl of the sample preparation.

The content of each cuvette is mixed and the measure of absorbance (A1) of the solutions is taken after approximately 2 mn in the spectrophotometer at 340 nm (spectrophotometer equipped with cuvettes with 1.0 cm of optical path, able to measure at a wavelength of 340 nm, and verified according to the procedure described in the related manufacturer's technical manual).

The reactions are then immediately initiated by adding 100 μl of solution no. 2, which corresponds to the OPA solution of bottle 2 of the Megazyme kit in each spectrophotometer cuvette.

The content of each cuvette is mixed and they are then placed in darkness for approximately 20 minutes.

The measure of absorbance $A_2$ of the blank, the standard and the sample are then taken from the spectrophotometer at 340 nm.

The free amino nitrogen content, expressed as percentage by weight relative to the weight of the product, is given by the following formula:

$$\%\ \text{amino nitrogen} = \frac{(\Delta Aech - \Delta Ablc) \times 3.15 \times 14.01 \times V \times 100}{6803 \times 0.05 \times m \times 1000}$$

$$\%\ \text{amino nitrogen} = \frac{(\Delta Aech - \Delta Ablc) \times 12.974 \times V}{m \times 1000}$$

where:

ΔAech=Aech2−Aech1

ΔAblc=Ablc2−Ablc1

Aech2=absorbance of the sample after adding solution no. 2

Aech1=absorbance of the sample after adding solution no. 1

Ablc2=absorbance of the blank after adding solution no. 2

Ablc1=absorbance of the blank after adding solution no. 1

V=volume of the flask m=weight of the test specimen in g

6803=extinction coefficient of the isoindole derivative at 340 nm (in $l \cdot mol^{-1} \cdot cm^{-1}$).

14.01=molar mass of the nitrogen (in $g \cdot mol^{-1}$)

3.15=final volume in the cuvette (in ml)

0.05=test specimen in the cuvette (in ml)

Determining the Content of Protein Nitrogen:

The content of protein nitrogen is determined according to the DUMAS method according to standard ISO 16634-2016. It is expressed as percentage by weight relative to the weight of the product.

Calculation of the Degree of Hydrolysis

The degree of hydrolysis (DH) is calculated with the following formula:

$$DH = \frac{\%\ \text{amino nitrogen}}{\%\ \text{protein nitrogen}} \times 100$$

Even more preferably, the water-soluble fraction according to the invention also comprises agmatine in a concentration between 10 ppm and 100 ppm expressed as dry weight of agmatine to dry weight of final product, preferentially between 10 ppm and 40 ppm on dry basis, preferentially between 15 ppm and 35 ppm, even more preferentially between 20 ppm and 30 ppm.

The term "agmatine", for the purposes of the present invention means the biogenic amine obtained from arginine by a chemical reaction referred to as decarboxylation. It is present in most of the tissues of our body, plants, meat and fish. This metabolic by-product of arginine is stored in the cells of the brain and spinal cord. Agmatine promotes the release of nitric oxide, a molecule involved in the relaxation of smooth muscle. It therefore helps to better manage stress. Any method known to a person skilled in the art is suitable for performing this assay. In particular, the method described in "Improved Method for HPLC Analysis of Polyamines, Agmatine and Aromatic Monoamines in Plant Tissue" (Robert D. Slocum & al., Plant Physiol. 1989 February; 89 (2): 512-517) is used The invention also relates to the process for obtaining this water-soluble fraction extracted from leguminous plants comprising the following steps:

1—Obtaining a water-soluble fraction of leguminous plants,
2—Optionally, desalinating the water-soluble fraction,
3—Fermenting the water-soluble fraction extracted from leguminous plants using a microorganism of the *Bacillus* genus,
4—Optionally, eliminating the microorganism,
5—Optionally, bacteriologically stabilizing the water-soluble fraction thus obtained.

The first step of the process according to the invention thus consists of obtaining a water-soluble fraction of leguminous plants.

Preferably, this first step is divided into two sub-steps:

i) Implementing leguminous plant seeds, with an optional pre-treatment;
ii) Wet separating the constituents of the leguminous plant seeds into 4 fractions: a starch fraction, a pulp fraction, a protein fraction of globulin type and a residual water-soluble fraction;

The first step i) of implementing the pea seeds consists of preparing for the next steps. The seeds can first undergo steps of cleaning, sieving (separating seeds from stones for example.). Then, the external fibers are separated from the seeds themselves (this step is also referred to as dehulling). Finally, the cotyledons obtained can undergo steps of soaking, bleaching, toasting. Preferably, if a bleaching step is performed, the protocol will be 3 min at 80° C.

The second step ii) is described in detail in patent application EP1400537, which is incorporated herein by reference. The pea seed is ground into meal and suspended in water. These two steps can be consecutive in a process referred to as "dry grinding" (grinding and suspension) or simultaneous in a process referred to as "wet grinding". The starch and the pulps (also referred to as internal fibers) are respectively eliminated using hydrocyclones and horizontal decanters. After eliminating these two insoluble compounds, the pH of the liquid supernatant obtained is acidified between 4 and 6, preferentially between 4.5 and 5, in order to precipitate the proteins referred to as "globulins" (representing about 80% of the total proteins), a heating between 50° C. and 80° C., preferentially between 60° C. and 70° C. can be applied consecutively in order to make the globulins coagulate with a maximum yield. The resulting coagulate is sent to centrifuges in order to separate the globulins in the form of a solid floc on the one hand and the residual water-soluble fraction in liquid form on the other. Any other wet extraction process that results in generating these 4 fractions—a starch fraction, a pulp fraction, a protein fraction of globulin type and a soluble fraction—may also be implemented in order to generate a water-soluble fraction. It is also possible to obtain a concentrate via a dry process (turbo-separation or air-classification) then to continue extracting the various fractions using a wet process.

Optionally, the water-soluble fraction of leguminous plants can also undergo several membrane filtration steps in order to reduce or even separate the protein fraction, which consists mostly of albumins. The albumins of the water-soluble fraction thus prepared will be reduced or even removed. Two water-soluble fractions are thus generated: an albumin fraction and a sugar fraction. This separation of the albumins from the water-soluble fraction is well known for example from the article "Pilot scale recovery of proteins from a pea whey discharge by ultrafiltration" (Gao & al. 2000) or else from patent application WO2014/118449. For this purpose, the use of an ultrafiltration with a cut-off threshold adapted to separate proteins and sugars is preferred. The sugar fraction will be used as raw material for the following steps. With these two distinct fractions (albumins and fermented sugars according to the invention), the albumin/sugar ratio can be more finely standardized by mixing the two fractions. The residual amounts can be recovered separately. According to one embodiment, the process for obtaining the water-soluble fraction extracted from leguminous plants according to the invention thus comprises the following steps:

1—Obtaining a water-soluble fraction of leguminous plants,
1bis—At least one membrane filtration of the water-soluble fraction
2—Optionally, desalinating the water-soluble fraction,
3—Fermenting the water-soluble fraction extracted from leguminous plants using a microorganism of the *Bacillus* genus,
4—Optionally, eliminating the microorganism,
5—Optionally, bacteriologically stabilizing the water-soluble fraction thus obtained.

The second step, which is optional, according to the invention consists of desalinating the water-soluble fraction of leguminous plants. For this purpose, any technique well-known to a person skilled in the art can be used, for example such as demineralization or precipitation. Preferably, a membrane separation such as ultrafiltration, nanofiltration or reverse osmosis will be used. The goal here is to separate the salts in the permeate and the rest of the water-soluble fraction in the retentate. Preferably, a nanofiltration with a cut-off threshold of about 500 Da, more precisely between 1 kDa and 250 Da, will be used. This optional step is recommended to get rid of the excessive amount of salt, in particular potassium. The water-soluble fraction is thus purified of its excess salts (about 80% on average) which concentrate in the permeate. The retentate is then used as raw material for the following steps.

The third step of the process according to the invention thus consists of fermenting the water-soluble fraction extracted from leguminous plants using a microorganism of the *Bacillus* genus, preferentially *Bacillus subtilis*, even more preferentially *Bacillus subtilis* Natto.

The term "fermentation", for the purposes of the invention means metabolic processes generally converting carbohydrates into acids, gases or alcohols in order to extract some of their chemical energy while re-oxidizing the coenzymes reduced by these reactions. This is a redox metabolic pathway in which the ultimate electron acceptor is often confused with the final product of the reactions. It is characterized by a partial degradation of the fermentable substance and allows only for a limited production of energy. It takes place in yeasts and bacteria, as well as in muscle cells lacking oxygen, that is under anaerobic conditions.

In the present invention, the fermentation is carried out in a liquid medium, so-called "submerged" fermentation. It is also possible to consider fermentation in a solid medium, even if this is much less efficient.

As it will be exemplified hereunder, the fermentation will be carried out preferentially with zero pO2, while adding oxygen to the fermentation medium directly in the liquid.

The term "pO2", as used in this invention, means the dissolved oxygen content that can be measured using a suitable probe conventionally used in industrial fermentation. This probe thus measures in real time the exact concentration of dissolved oxygen in the fermentation medium. Note that the pO2 can be zero even while air or oxygen are being sent in parallel to the fermenter. The introduced oxygen is then immediately metabolized by the microorganism of the *Bacillus* genus.

Preferably, the addition of oxygen will be done by introducing an air flow of between 0.03 VVM and 0.5 VVM, preferentially between 0.1 VVM and 0.4 VVM, even more preferentially between 0.2 VVM and 0.3 VVM, 0.25 VVM being the preferentially targeted value.

The term "VVM", for the purposes of the present invention means the quantification of a gas flow rate, preferentially of air or pure oxygen, introduced into a fermenter. 1 VVM means 1 Volume of gas per Volume of fermenter per Minute. More specifically, for a fermenter of one $m^3$, 1 VVM means 1 $m^3$ of gas per minute.

Preferably, the fermentation pH is rectified or regulated between 5.5 and 6.5; preferentially 6. Indeed, as shown in the example section, a fermentation pH above 6.5 will result in the overproduction of lactic acid.

Preferably, the fermentation temperature is between 30° C. and 40° C., preferentially between 32° C. and 37° C., even more preferentially 37° C.

Even more preferably, the fermentation of the water-soluble fraction extracted from leguminous plants is carried out with a fermentation medium composed only of said water-soluble fraction. Indeed, it can be possible to add different carbon (e.g. glucose, fructose, starch) and amino (e.g. ammonia, yeast extract, ammonium sulfate, casein, whey, soy protein) substrates to the fermentation medium. In this case, the strains performing the fermentation will consume in a competitive or even preferential way, the different substrates added. The defructosylation will be less efficient, less complete or even not carried out at all. Similarly, the proteins can be hydrolyzed. The addition of chemical compounds (such as ammonium sulfate) or allergenic compounds (such as soy or casein) must be indicated to the final consumers, which could have major effects on the marketing thereof.

Preferably, the fermentation medium does not contain glucose and/or ammonium sulfate intentionally added to the water-soluble fraction.

Without being bound by any theory, the applicant noted that it was essential for the invention to carry out aerobic fermentation while limiting the addition of oxygen, at the risk of either producing too much organic acid, including lactic acid, or of causing the appearance of excessive foam requiring the excessive addition of antifoaming agent to control it. In the latter case, the antifoaming agent represents about 20% of the final solids, which is prohibitive for all food applications. The goal is not only to defructosylate the sugars, but to do so while limiting the presence of lactic acid and/or antifoaming agent, avoiding protein hydrolysis and promoting the synthesis of agmatine.

The term "microorganism", for the purposes of the invention means a living organism, invisible to the naked eye, which can only be observed using a microscope. Microorganisms are represented by various lifeforms, including bacteria, some microscopic fungi, archaebacteria, protists, microscopic green algae, plankton animals, planaria, amoebae, etc. In the present invention, the microorganisms are bacteria, preferentially of the *Bacillus* genus.

The term "*Bacillus*", for the purposes of the invention means the genus of gram-positive bacteria, belonging to the Bacillaceae family (Bacillaceae), the Bacillales order (Bacillales), the *Bacillus* class (Bacillis), the Firmicutes phylum (Firmicutes). These bacteria are bacilli and vary in size from (0.5×1.2 μm) to (2.5×10 μm). They are aerobic or facultative aero-anaerobic, and derive their energy through respiration or fermentation. These bacteria are able to produce endospores that allow them to withstand adverse environmental conditions. They will give birth to new bacteria if conditions are favorable. *Bacillus* are heterotrophic, saprophytic and ubiquitous. They are frequently found in soil, where some species have a role in the carbon and nitrogen cycle. *Bacillus* can be found in foodstuffs.

As *Bacillus subtilis* that are particularly suitable for the invention, *Bacillus subtilis* NRC33a or else *Bacillus subtilis* CCT 7712 can be cited, both of which are strains that are described in the literature.

Preferably, the fermentation of the water-soluble fraction extracted from leguminous plants by means of a microorganism of the *Bacillus* genus is carried out using the strain of *Bacillus subtilis* as filed with the CNCM on May 28, 2020 under number CNCM I-5515. This strain was deposited according to the Budapest treaty with the CNCM of the Pasteur Institute. The CNCM is the French National Collection of Microorganism Cultures of the Pasteur Institute, located at 25 rue du Docteur Roux, F-75724 Paris cedex 15.

In more general terms, without being bound by any theory, it is important for the strain to have an enzyme named levansucrase in its enzyme pool. It is thus possible to consider microorganisms other than those of the *Bacillus* genus, which remain however those that give the best results.

The term "levansucrase", for the purposes of the present invention means the enzyme sucrose: 2,6-beta-D-fructan 6-beta-D-fructosyltransferase (EC 2.4.1.10) that catalyzes the following reaction: sucrose+(2,6-beta-D-fructosyl)n→glucose+(2,6-beta-D-fructosyl)n+1. This enzyme belongs to the glycosyltransferase family, especially to the hexosyltransferases.

The use of a levansucrase extracted from a culture is possible, conventionally, in solution in a reactor, or in a column in the form of an immobilized enzyme. In this particular case, no agmatine will be produced.

The optional fourth step of the process according to the invention consists of eliminating the microorganism. The term "eliminating" preferentially means inactivating the microorganism, that is an operation aimed at inhibiting the biochemical processes that allow fermentation and/or reproduction. This can be achieved by using the different options that are well known to a person skilled in the art, such as sterilization, pasteurization or membrane filtration. Preferably, a person skilled in the art will use pasteurization, which allows the inactivation of the microorganism while preserving the labile molecules present. Even more preferably, a person skilled in the art would use centrifugation, which makes it possible to eliminate the microorganism without heating.

Preferably, a person skilled in the art, by leaving the microorganism and/or its spores, enriches the water-soluble fraction according to the invention with a strain and/or its spores with probiotic and/or postbiotic (inactivated probiotic) value.

The optional fifth and final step consists of stabilizing, preferentially by drying, the water-soluble fraction thus obtained. Any technique that is well-known to a person skilled in the art is used. Preferably, they will use atomization, preferentially multiple-effect atomization. Alternatively and optionally, they will concentrate the soluble fraction under vacuum to a solids content of between 40% and 60%, preferentially 50%.

The invention finally relates to the use of this water-soluble fraction of leguminous plants according to the invention in industry, particularly in the human and/or animal nutrition industries.

The invention also relates to a strain of *Bacillus subtilis* as filed with the CNCM on May 28, 2020 under number 1-5515.

The invention also relates to the use of a strain of *Bacillus subtilis* as filed with the CNCM on May 28, 2020 under number 1-5515 for the fermentation of carbohydrates, especially oligosaccharides, more particularly chosen from raffinose, stachyose and verbascose.

The invention will be better understood by means of the following nonlimiting examples.

EXAMPLES

Example 1: Production of a Water-Soluble Fraction as Raw Material

Pea seeds are used for this example. After dehulling the external fibers using a hammer mill, the cotyledons obtained are ground to produce a meal. 1,044 kg of meal suspension containing 25% by weight of solids (thus 261 kg of dry meal) are then introduced with 500 kg of water into a hydrocyclone array adapted from an industrial potato starch processing unit. This separation leads to the production of a light phase consisting of the mixture of protein, internal fibers and soluble matter. The heavy phase, containing the starch, is discarded.

The light phase at the hydrocyclone outlet contains as a mixture (142 kg of solids in total): the fibers (about 14.8% by weight, that is 21 kg of solids), the proteins (about 42.8% by weight, that is 60.8 kg of solids) and soluble matter (about 42.4% by weight, that is 60.2 kg of solids). It is then brought to a solids content of 11.4%. The fibers are separated out on centrifugal decanters of WESPHALIA type used in an industrial potato starch processing unit. The light phase at the outlet of the centrifugal decanter contains a mixture of proteins and of soluble matter, while the heavy phase contains the pea fibers. The heavy phase contains 105 kg of fibers with a solids content of 20%. It is noted that virtually all of the fibers are indeed found in this fraction. This fraction will be referred to hereinbelow as the "internal pea fibers" and corresponds to the pulp fraction.

As for the light fraction, it contains 1142 kg of a dissolved mixture of soluble matter and proteins. The proteins are coagulated at their isoelectric point by adjusting the light phase at the outlet of the centrifugal decanter to a pH of 4.6 and heating this solution to 70° C. for 20 min. After precipitation of the proteins, the sediment, containing 56 kg of proteins (86% of N 6.25 on a dry basis) is discarded. The liquid fraction, which will be referred to as "water-soluble fraction" is concentrated by vacuum evaporation to about 30% by weight of solids.

The non-defructosylated GOS content is 22.9 g/100 g solids.

The protein content is 30.1 g/100 g solids.

The degree of hydrolysis (or DH) of these proteins is calculated according to the OPA method, for which the protocol is described in the present application. This DH is equal to 11.

Example 2: Fermentation of the Water-Soluble Fraction Obtained in Example 1 with a Method Outside the Invention (Aeration Through the Fermenter Dome)

A *Bacillus subtilis* strain, as filed with the CNCM under number CNCM 1-5515, is used to ferment the water-soluble fraction.

A 5 ml cryotube containing 108 UFC/ml is used to inoculate a 2 l erlen with baffles containing 500 ml of LB medium (Tryptone (Bacto Trypton) 10 g/l, yeast extract (BactoYest Extract) 5 g/l and sodium chloride (NaCl) 10 g/l, sterilization for 20 min at 120° C.). This erlen is incubated at 37° C. while stirring at 150 RPM for 4.5 hours.

The production is carried out in a fermenter with a volume of 15 l after inoculation (7% preculture), The fermentation parameters are as follows: the stirring is set at 300 RPM (rotations per minute); air flow rate=4 l/min in the fermenter head. The pH is adjusted to 7 by adding 25% sodium hydroxide. The temperature is adjusted to 37° C.

The pO2 was not monitored because of the aeration on the surface of the medium: the principle of aeration through the fermenter dome results in the pO2 of the fermentation medium being zero. A first growth phase can be distinguished by observing the CPR (CPR means the amount of CO2 emitted by the strain) which increases from the start of fermentation up to 15 h and then decreases at 30 h. This emission of CO2 shows that the metabolism of the strain during this fermentation was fermentative and that it did not use the oxygen in the air or used very little of it. Then a second growth phase which starts at 30 h until the end of fermentation, at 40 h. This diauxy phenomenon is further observed by the profile of the base addition.

The wort from the production fermenter is atomized. The first step is to centrifuge (30000 G, 20 min) in order to recover the supernatant, then the latter is evaporated to reach about 10% of solids and ensure correct atomization. The atomization parameters are as follows: Input T° C. 190° C., output T° C. 110° C.

The evolution of the different sugars is monitored by thin layer chromatography (TLC) and by HPLC (HPAEC-PAD), at T=0 h, the presence of raffinose, stachyose and verbascose, which form the GOS (galacto-oligosaccharides), is observed. Monitoring checks were carried out at 19 h, 24 h and 42 h of fermentation. It can be seen that the GOS are progressively and completely defructosylated. The raffinose is transformed into melibiose, the stachyose into manninotriose and the verbascose into verbascotetraose. The sucrose is entirely consumed.

The amino acid profile is rather well preserved, with the exception of the arginine. This amino acid profile is obtained by protein hydrolysis and conventional HPLC analysis well known to a person skilled in the art.

An analysis of the organic acids produced by HPLC shows a high content of organic acids including 12% on dry basis of lactic acid, which is too high for some applications, without considering additional purification.

The conclusion can thus be drawn that defructosylation takes place correctly, without significant foaming, but the production of lactic acid up to 12% is an additional handicap.

The defructosylated GOS content is 16.5%.

The protein content is 29.8%.

Example 3: Fermentation of the Water-Soluble Fraction According to the Invention with a Process Outside the Invention (Conventional Aeration in the Fermentation Medium, with pO2 Control)

A *Bacillus subtilis* strain, as filed with the CNCM under number CNCM 1-5515, is used to ferment the water-soluble fraction.

A 5 ml cryotube containing 108 UFC/ml is used to inoculate a 2 l erlen with baffles containing 500 ml of LB medium (Tryptone (Bacto Trypton) 10 g/l, yeast extract (BactoYest Extract) 5 g/l and sodium chloride (NaCl) 10 g/l, sterilization for 20 min at 120° C.). This erlen is incubated at 37° C. while stirring at 150 RPM for 4.5 hours.

The production is carried out in a fermenter with a volume of 15 l after inoculation (10% preculture), the fermentation parameters are as follows: The pO2 is regulated at 30% in cascade on stirring (that is pO2 regulation using the stirring), the minimum stirring is 400 RPM; air flow rate of 1 VVM, sent directly into the liquid medium. The pH is adjusted to 7 by adding 25% sodium hydroxide. The temperature is adjusted to 37° C.

No adaptation time is observed. The pO2 drops very quickly from 100% to 30% in 4 h. After 2 h of production, foam forms and a massive amount of antifoaming agent is added to the medium via a suitable pump. Without this antifoaming agent, the fermenter empties completely (carried out in preliminary tests). This addition, which is quantified by weighing, is constant until 13 hours of fermentation, at which time the pO2 rises rapidly. Then the latter stagnates at 80% between 15 h and 20 h of fermentation, which could indicate a diauxy phase. A pO2 greater than 30% could be maintained without increasing agitation. The gas analysis confirms the observations made above on the diauxy.

The wort from the production fermenter is atomized. The first step is to centrifuge (30000 G, 20 min) in order to recover the supernatant, then the latter is evaporated to reach about 10% of solids and ensure correct atomization. The atomization parameters are as follows: Input T° C. 190° C., output T° C. 110° C.

The evolution of the different sugars is monitored by thin layer chromatography (TLC) and by HPLC (HPAEC-PAD), at T=0 h, the presence of raffinose, stachyose and verbascose, which form the GOS, is observed. Checks were carried out at 19 h, 24 h and 42 h of fermentation. It can be seen that after 19 h, the GOS are progressively and completely defructosylated. The raffinose is transformed into melibiose, the stachyose into manninotriose and the verbascose into verbascotetraose. The sucrose is entirely consumed.

As shown in FIG. 1, the amino acid profile is particularly modified, with loss of a significant amount thereof. This amino acid profile is obtained by protein hydrolysis and conventional HPLC analysis well known to the person skilled in the art.

The GOS content is 17.5%

The protein content is 26.1%.

The degree of hydrolysis (or DH) is also calculated according to the OPA method, for which the protocol is described in the present application. This DH is equal to 20.5.

By performing a mass balance of the substrates used and the quantities of antifoaming agent sent to the fermenter, the final amount of antifoaming agent in the fermenter is estimated to be about 20%. This amount is far too large to consider direct recovery without purifying this fraction.

The loss of amino acids, the increase in DH and the residual amount of antifoaming agent rule out this production method, which alters the nutritional quality, despite the defructosylation.

Example 4: Fermentation of the Water-Soluble Fraction with a Process According to the Invention by Aeration in the Fermentation Medium, with Controlled Aeration Rate and Zero pO2

A *Bacillus subtilis* strain, as filed with the CNCM under number CNCM I-5515, is used to ferment the water-soluble fraction.

A 5 ml cryotube containing $10^8$ UFC/ml is used to inoculate a 2 l erlen with baffles containing 500 ml of LB medium (Tryptone (Bacto Trypton) 10 g/l, yeast extract (BactoYest Extract) 5 g/l and sodium chloride (NaCl) 10 g/l, sterilization for 20 min at 120° C.). This erlen is incubated at 37° C. while stirring at 150 RPM for 4.5 hours.

The production is carried out in a fermenter with a volume of 15 l after inoculation (10% preculture), the fermentation parameters are as follows: Air flow rate of 0.25 VVM, without control of the pO2 directly in the liquid medium. The stirring is set to 300 RPM. The pH is rectified to 6 with sodium hydroxide and hydrochloric acid but is not regulated afterwards.

No adaptation time is observed. The pO2 drops very quickly to remain zero until the end of fermentation. The pH rectified to 6 remains unchanged. The fermentation is carried out during 42 h, with samples collected at various times during the fermentation.

The wort from the production fermenter is atomized. The first step is to centrifuge (30000 G, 20 min) in order to recover the supernatant, then the latter is evaporated to reach about 10% of solids and ensure correct atomization. The atomization parameters are as follows: Input T° C. 190° C., output T° C. 110° C.

The evolution of the different sugars is monitored by thin layer chromatography (TLC) and by HPLC (HPAEC-PAD) at T=0 h, the presence of raffinose, stachyose and verbascose, which form the GOS, is observed. Checks were carried out at 19 h, 24 h and 42 h of fermentation. It can be seen that after 19 h, these GOS are completely defructosylated. The raffinose is transformed into melibiose, the stachyose into manninotriose and the verbascose into verbascotetraose. The sucrose is entirely consumed.

The lactic acid content analyzed by HPLC is titrated at 1% dry weight of lactic acid per total weight. In an alternative test similar in every way to the latter differing only in that the pH of the fermentation was rectified to 7 instead of 6, the lactic acid content was titrated at 5%.

The amino acid profile, also obtained by HPLC, is conserved.

The GOS content is 18.3%.

The protein content is 30.5%.

The degree of hydrolysis (or DH) is calculated according to the OPA method, for which the protocol is described in the present application. This DH is equal to 11.5.

Example 5: Defructosylation of the Prior Art with an Invertase According to Patent Application WO2010/109093

The water-soluble pea fraction is adjusted to 15% by weight of solids and filtered by means of an ultrafiltration membrane, with a cut-off threshold set at 5,000 Da, in order to clarify it and remove the proteins. This step is followed by a concentration of the permeate by reverse osmosis, to bring it to 20% by weight of solids.

At the same time, 100 ml of a 1 mg/ml invertase solution is prepared, which is then also washed by centrifugation for 30 minutes. The pellet is taken up with 50 ml of water. 980 ml of the pea fraction is then mixed with 50 ml of the enzyme solution in a double-walled stirred reactor placed in a water bath at 50° C. The hydrolysis is monitored by assaying the reducing sugars with an aqueous alkaline solution of 3,5-dinitrosalicylic acid (DNS) at different time intervals. After at least 12 hours of hydrolysis, the enzyme is neutralized, then the product obtained is centrifuged and filtered to obtain a clear solution that is then concentrated by rotary evaporation under vacuum at 70° C., until a clear liquor is obtained.

An analysis of the total fructose in the product obtained shows a very high fructose content, about 10%.

The invention claimed is:

1. A water-soluble fraction extracted from leguminous plants comprising between 10% and 30% of defructosylated oligosaccharides and between 20% and 40% of proteins, the percentages being expressed in dry weight relative to the total weight of solids.

2. The water-soluble fraction extracted from leguminous plants according to claim 1, wherein the leguminous plants are selected from the list consisting of pea and *faba* bean.

3. The water-soluble fraction extracted from leguminous plants according to claim 1, wherein it comprises between 10% and 30% of defructosylated oligosaccharides selected from the list consisting of melibiose, manninotriose and manninotetraose.

4. The water-soluble fraction extracted from leguminous plants according to claim 1, wherein it contains less than 2% of fructose, the percentages being expressed by weight relative to the total weight of solids.

5. The water-soluble fraction extracted from leguminous plants according to claim 1, wherein it contains between 0.25% and 1% by weight of lactate, the percentages being expressed by weight relative to the total weight of solids.

6. The water-soluble fraction extracted from leguminous plants according to claim 1, wherein it contains between 20% and 40% of proteins characterized as albumins.

7. The water-soluble fraction extracted from leguminous plants according to claim 1, wherein it has proteins, the degree of hydrolysis of which, or DH, is less than 20.

8. The water-soluble fraction extracted from leguminous plants according to claim 1, wherein it also comprises agmatine in a concentration of between 10 ppm and 100 ppm expressed as dry weight of agmatine to dry weight of final product.

9. A process for obtaining a water-soluble fraction extracted from leguminous plants comprising between 10% and 30% of defructosylated oligosaccharides and between 20% and 40% of proteins, said process comprising the following steps:

1—Obtaining a water-soluble fraction of leguminous plants,

2—Optionally, desalinating the water-soluble fraction,

3—Fermenting the water-soluble fraction extracted from leguminous plants using a microorganism of the *Bacillus* genus, preferably *Bacillus subtilis,*

4—Optionally, eliminating the microorganism,

5—Optionally, bacteriologically stabilizing the water-soluble fraction thus obtained.

10. The process according to claim 9, wherein the water-soluble fraction of step 1 is obtained by the following process:

i) Implementing leguminous plant seeds, with an optional pre-treatment;

ii) Wet separating the constituents of the leguminous plant seeds into 4 fractions: a starch fraction, a pulp fraction, a protein fraction of globulin type and a residual water-soluble fraction.

11. The process according to claim 9, wherein the fermentation according to step 3 is carried out with zero pO2, while adding oxygen to the fermentation medium directly into the liquid.

12. The process according to claim 9, wherein the fermentation medium of step 3 comprises only the water-soluble fraction of leguminous plants.

13. The process according to claim 9, wherein the fermentation step of step 3 is carried out by introducing an air flow of between 0.03 VVM and 0.5 VVM.

14. The process according to claim 9, wherein the pH of the fermentation is rectified or adjusted between 5.5 and 6.5.

15. The process according to claim 9, wherein the fermentation step is carried out using the strain of *Bacillus subtilis* as deposited with the CNCM on May 28, 2020 under number CNCM I-5515.

* * * * *